United States Patent [19]

Meno

[11] Patent Number: 4,716,904
[45] Date of Patent: Jan. 5, 1988

[54] HEART OUTPUT AND CIRCULATORY IMPEDANCE MEASURING METHOD AND APPARATUS

[75] Inventor: Frank Meno, Pittsburgh, Pa.

[73] Assignee: University of Pittsburgh of The Commonwealth System of Higher Education, Pittsburgh, Pa.

[21] Appl. No.: 877,149

[22] Filed: Jun. 23, 1986

[51] Int. Cl.⁴ ............................................. A61B 6/00
[52] U.S. Cl. ..................................... 128/654; 128/659; 128/695; 128/713; 358/111
[58] Field of Search ............... 128/713, 670, 695, 653, 128/654, 659; 358/111

[56] References Cited

U.S. PATENT DOCUMENTS

| | | | |
|---|---|---|---|
| 4,101,961 | 7/1978 | Reiber | 128/695 |
| 4,204,255 | 5/1980 | Mistretta | 358/111 |
| 4,240,440 | 12/1980 | Groch et al. | 128/654 |
| 4,398,213 | 8/1983 | Haendle et al. | 358/111 |
| 4,399,457 | 8/1983 | Riederer et al. | 358/111 |
| 4,418,387 | 11/1983 | Yamaguchi et al. | 364/414 |
| 4,422,146 | 12/1983 | Yamaguchi et al. | 364/414 |
| 4,430,749 | 2/1984 | Schardt | 382/54 |
| 4,447,827 | 5/1984 | Alexandrescu et al. | 358/111 |
| 4,450,478 | 5/1984 | Ledley | 358/111 |
| 4,458,688 | 7/1984 | Von Behren | 128/659 |
| 4,503,459 | 3/1985 | Haendle et al. | 358/111 |

FOREIGN PATENT DOCUMENTS 2409173  9/1975  Fed. Rep. of Germany ...... 128/695

Primary Examiner—Edward M. Coven
Assistant Examiner—Ruth S. Smith
Attorney, Agent, or Firm—Arnold B. Silverman; Joyce L. Morrison

[57] ABSTRACT

The invention shows a heart output and circulatory impedance measuring method and associated apparatus based on consecutive subtraction and synchronous summation of digitized ventriculographic images which effectively distinguishes between the motion resulting from contraction of the heart, and the motion resulting from actual displacement or physical movement of the heart back and forth within the chest cavity. From these data is computed a decrement in ventricular volume yielding, in time with subsequent images, the amount of blood ejected from the ventricle that represents the flow. By simultaneously recording the ventricular pressure and by synchronously dividing the pressure by the flow, ventricular load impedance is obtained.

15 Claims, 5 Drawing Figures

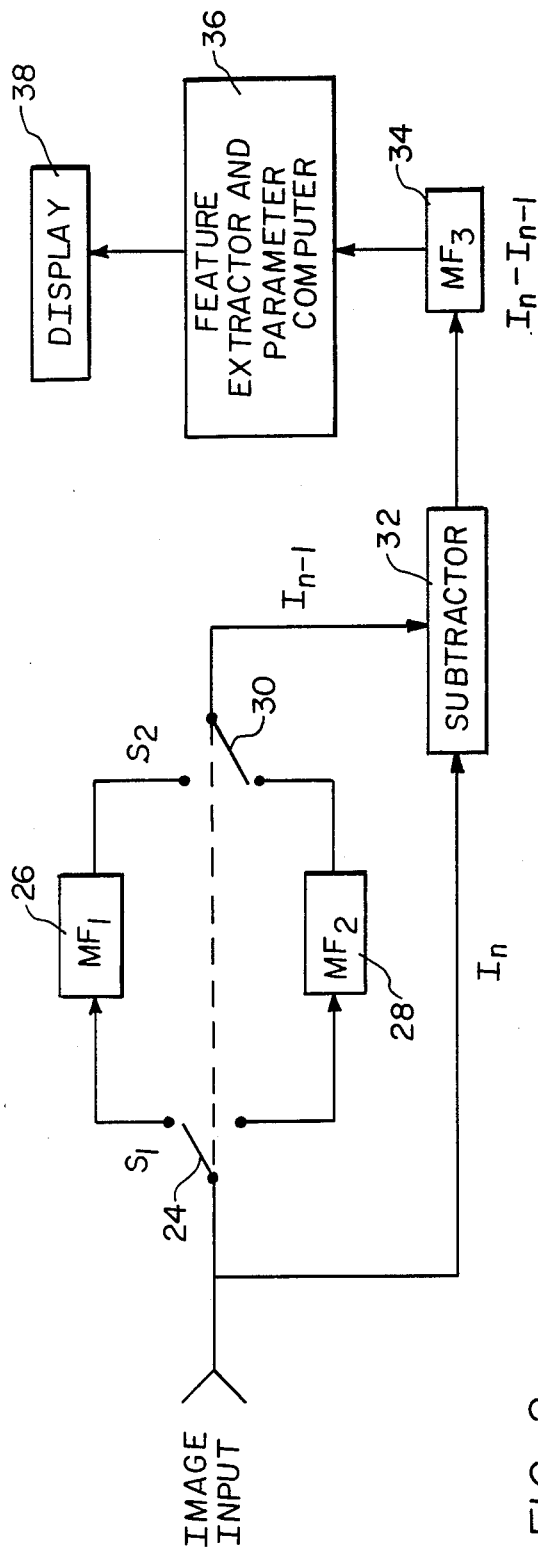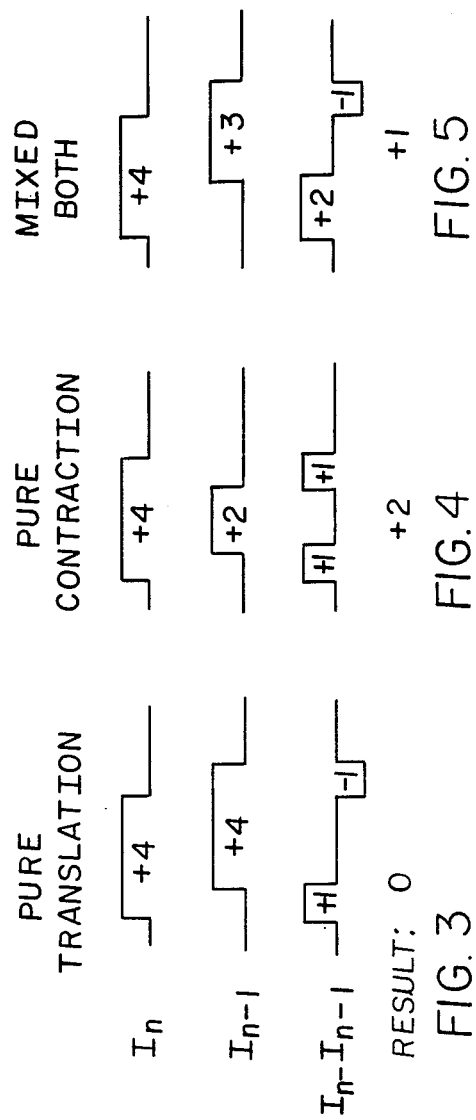

HEART OUTPUT AND CIRCULATORY IMPEDANCE MEASURING METHOD AND APPARATUS

BACKGROUND OF THE INVENTION

1. Field of the Invention

This invention relates to a heart output and circulatory impedance measuring method and apparatus.

2. Description of the Prior Art

It has been known to use radiographic devices to produce radiographic images of the cardiovascular system. See generally U.S. Pat. Nos. 4,204,225; 4,422,146; 4,418,387; and 4,430,749. Various radiographic systems have been designed to show the movement of objects. See U.S. Pat. Nos. 4,204,225; 4,430,749; 4,447,827; and 4,450,478. Subtraction of radiographic images has also been known. See, for example, U.S. Pat. Nos. 4,458,688; 4,398,213; 4,503,459; and 4,399,457.

One of the most widely used methods, sometimes known as ventriculometry, relies on off-line human interaction namely, requiring an operator to carefully outline the ventricular boundary on a cine projection. This is a very time consuming process, and does not yield immediate on-line results which are valuable for studying therapeutic interventions.

The major difficulty in automating ventriculometry is separating the components of ventricular contraction from its displacement during each beat. The heart does not merely contract, but it also moves and rotates at the same time. These additional translation type motions as distinguished from heart contraction, can introduce substantial errors in volume computation, and, may be difficult to handle without human interaction.

Another method for ventricular volume computation, called densitometry, does not delineate the outline of the ventricle, but merely measures the amount of contrast medium contained in the ventricle. This method does not yield very dependable results, mostly due to the fact that the measuring procedure cannot effectively separate the contributions from the medium located in the ventricle and that which has been ejected into the adjacent circulatory system.

In spite of these prior disclosures, there remains a need for a cardiac output and circulatory impedance measuring system and method that efficiently measures these characteristics.

SUMMARY OF THE PRESENT INVENTION

The present invention has met the above-described need by providing a heart output and circulatory impedance measuring apparatus and method. The method of measuring heart output uses pulsed X-ray beams that pass through the heart or a heart chamber, such as the ventricle, filled with a contrast medium and blood. The portion of the X-ray beams that are not absorbed by the chest and the heart are detected and produce an image. These images are converted into electrical signals. These signals may be analog or digital signals. The image signals detected at one time are subtracted from those detected at another time. Subsequently, the gray scale values of the pixels in the subtracted images are summed over the whole image, yielding a number that is proportional to the amount of contraction. The signals relating to heart displacement are cancelled. The heart contraction signals are converted into a corresponding volume of blood pumped by the heart in a predetermined time interval.

The apparatus for determining heart output has an X-ray source means that provides a pulsed source of X-rays that impinge on the heart. Detection means receive the X-rays from the heart. Digital processor means that first create digital signals related to heart images at different times, and second, digital signals that are related only to heart contractions at different times. The digital processor subtracts and sums these digital signals so as to separate the heart displacement signals from the heart contraction signals, and then computes instantaneous volumes. The above operations could also be performed in an analog manner.

It is an object of the present invention to provide a heart output and circulatory impedance measuring apparatus that measures heart contractions.

It is also an object of the present invention to provide an improved heart output and circulatory impedance measuring apparatus based on dividing ventricular pressure by the ejection flow.

It is an object of the present invention to provide a heart output and circulatory impedance apparatus working in real time.

It is an object of the present invention to provide a rapid real-time system for measuring heart performance.

It is a further object of the present invention to employ subtraction of time displaced images in conjunction with pixel summation to separate cardiac contractions from cardiac displacement.

It is an object of the present invention to provide such a system which operates in a manner which is consistent with existing radiographic procedures.

These and other subjects of the present invention will be more fully understood from the following description of the invention with reference to the illustrations appended hereto.

BRIEF DESCRIPTION OF THE DRAWINGS

FIG. 2 is a more detailed schematic illustration of a subsystem of the invention.

FIG. 3 shows plots of gray scale versus distance in an image depicting pure translation taken at two different times.

FIG. 4 shows plots of gray scale versus distance in an image depicting pure contraction taken at two different times.

FIG. 5 shows plots of a mixture of the examples presented in FIGS. 3 and 4.

DESCRIPTION OF THE PREFERRED EMBODIMENTS

Figure 1:
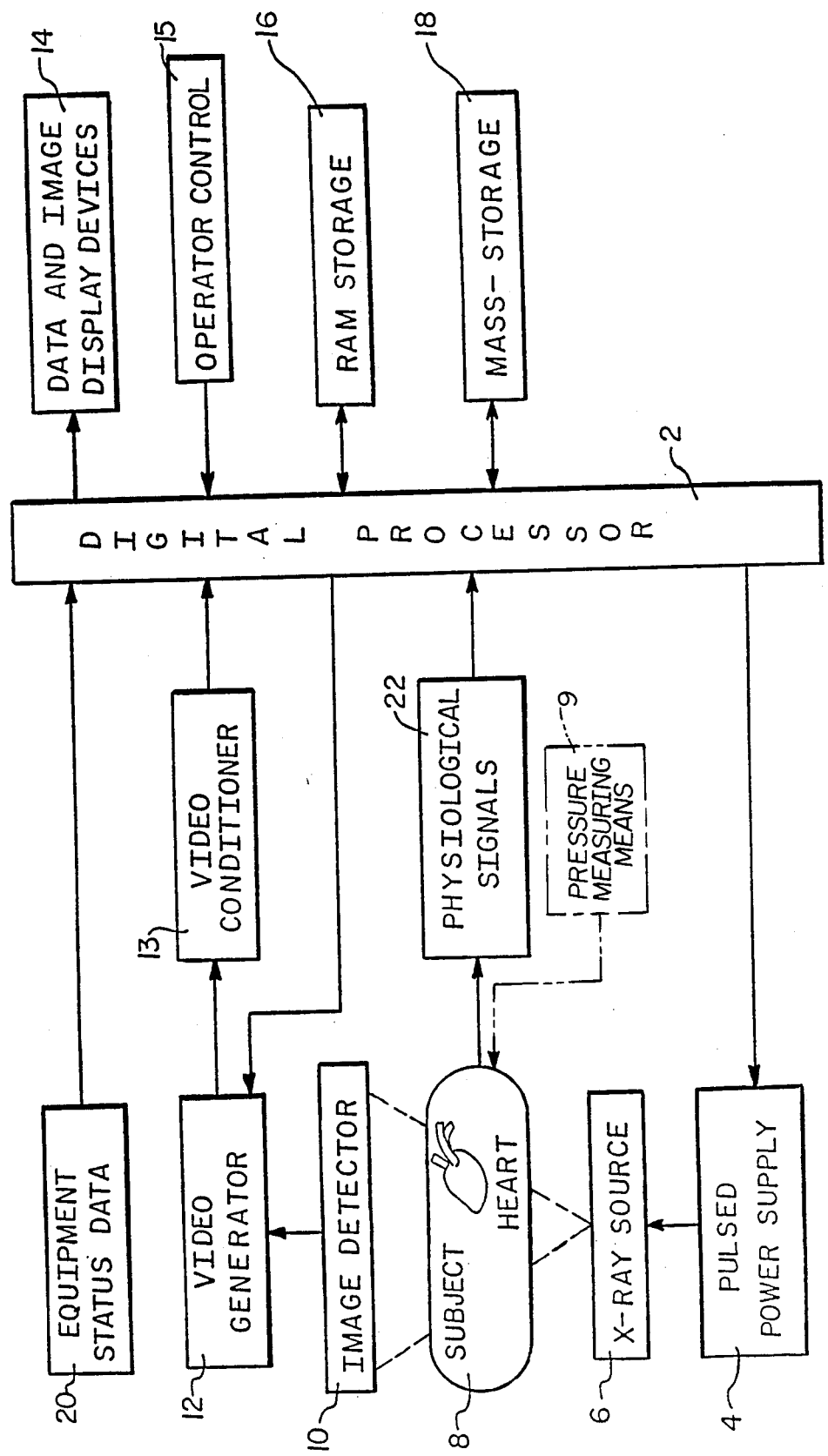
FIG. 1 is a schematic illustration of an embodiment of the invention.

The present invention discloses a method for utilizing images derived from X-rays to effect subtraction and summation so that the resulting numerical values represent only contraction of the heart. In order to determine blood flow from the heart into the aorta, it is necessary to compute many times each second the amount of blood ejected by the left ventricle. This invention deals with a novel automated approach in using left ventriculograms in conjunction with digital video image processing. The invention is an improvement in that it permits image processing which effectively distinguishes between the motion resulting from contraction of the heart, and the motion resulting from actual displacement or physical movement of the heart back and forth within the chest cavity.

In particular, when the heart pumps, it moves from an enlarged full condition to a reduced size which can be related to the volume of blood pumped. In addition, when the heart pumps there is physical movement of a displacement type. The present system subtracts one image from another and sums the pixels so that all movements which are attributable to displacement can be eliminated, thereby permitting a direct measurement of change in heart size. This will permit determination of the volume of blood pumped. In one approach, the image data will be presented to a computer and converted to digitized information and the subtraction, summation, and other operations will be effected electronically to compute the magnitude of a contraction.

Prior art methods do not distinguish between heart movement alone and contraction alone. The invention uses a subtraction and summation technique that is time difference and area sum related to compute ventricular volume to isolate the physical displacement of the heart from the pumping action of the heart.

Referring to FIG. 1 in greater detail, the digital processor means 2 causes the pulsed power supply 4 to energize an X-ray source means 6. The X-ray source means 6 may be a single source, two X-ray sources or more. The digital processor means 2 may readily be created and programmed by one skilled in the art to perform the functions set forth herein and need not be disclosed in great detail. The X-ray source means 6, in the embodiment shown in FIG. 1, emits a conical beam which passes through the heart 8. The portion of the beam which passes through the chest and heart 8 is then received by an image detector or detection means 10 which transforms the X-ray beam information into signals which are passed to a video generator 12, which can consist of an X-ray screen, image intensifier and a TV camera.

The image detector or detection means 10 or two image detectors, if there are two X-ray sources, is located perpendicular to the X-ray sources. These signals are transformed by correction of the gray scale and digitized in the video conditioner 13, and pass to the digital processor means 2.

The video generator 12 may be a type of television camera or any other suitable means for converting the X-ray images into corresponding electrical signals. The video conditioner 13 serves to transform the video signal into a desirable form. The digital processor means 2 may be a digital or analog computer that is programmed to effect the desired computations and control the operation of the other elements of the system. For example, the digital processor means 2 creates digital signals related to heart contraction at different times; the digital processor means 2 has means for subtracting and summing the digital signals for effecting the separation of heart displacement signals from heart contraction signals. These contraction signals may then be converted into volume of blood pumped by the heart.

The digital processor means 2 then passes the information to data and image display device 14, RAM storage unit 16 and/or mass-storage unit 18. The display device 14 cooperates with the digital processor means to display information related to heart contraction signals. The digital processor means 2 also receives information on the equipment status 20, as well as physiological signals 22 from the heart 8 and patient. The entire apparatus is under operator control 15. The RAM storage unit 16 stores the digitized images during processing and display on image display device 14. The mass storage unit 18 may be any suitable storage unit such as a disk or tape unit.

FIG. 2 represents a basic function block diagram for digital image subtraction. $S_1 24$ and $S_2 30$ are synchronous switches. For purposes of illustration, $MF_1 26$ is the memory holding odd number images and $MF_2 28$ is the memory holding even number images. However, $MF_1 26$ memory and $MF_2 28$ memory can be reversed. $MF_3 34$ is the memory holding the "difference images" or $I_n - I_{n-1}$. The image input flows through switch $S_1 24$, where the information $I_n$ is stored in $MF_1 26$, and at the same time is fed to the subtractor 32. At the same time, the image $I_{n-1}$ is read out synchronously from $MF_2 28$, where it was stored, and passes through $S_2 30$ also to the subtractor 32. The synchronously subtracted information from $MF_2 28$ containing image $I_{n-1}$ and the current image $I_n$, is then sent to $MF_3 34$ where the results are stored. This operation is performed repeatedly on all subsequent images.

The feature extractor and parameter computer 36 sums the resulting difference pixels from $MF_3 34$ for the entire image of the heart. Other arithmetic operations relating to the geometry of the image are performed at this point and will be described in detail hereinafter. The display 38 may be a visual display or may be a storage unit for the computed results.

In general, it will be contemplated that the images may be obtained along two generally perpendicular axes in order to permit a more accurate determination by providing two sets of images which are offset from each other by about 90°. This system is also advantageous in that it may be adapted to operate in real time.

The proposed measurement technique for heart output is based upon point by point contrast subtraction, normalization and delineation in sequential fluoroscopic images and thereafter, integration of contrast over the whole resulting image. This numerical quantity will be proportional to the amount of area contraction of the heart image, thus providing a measure for the amount of contraction during the time elapsed between the two "snapshot" images in question. By established computational techniques, the contraction area may be related to the volume change and hence output flow. If bi-plane or multiple projections are used, the accuracy of the computed flow may be increased. This method is extremely advantageous in that it may be used without human interaction and substantially eliminates the difficulties associated with the discrimination between heart displacement and contraction.

During ventriculography, based on pulsed fluoroscopy, any two successive digitized video images are subtracted in real time. These "difference images" or $I_n - I_{n-1}$ contain only those aspects of the image that have changed, that is, registering only the amount of contraction and motion. If the time between successive images is relatively short, 1/30 of a second for example, then the motion due to respiration is negligible and does not contribute significantly to error.

The "difference image" contains not only information on the amount of motion, but also on its direction by registering higher or lower values on the deviation from mid-range gray scale. Thus, if an object merely moves, the leading and trailing edges in a "difference image" register with opposite gray scale deviations, whereas a contraction or expansion is registered by gray scale deviations in the same direction.

In order to remove ambiguities in the outline of the ventricle, the relatively noisy "difference image" will be automatically thresholded, and the boundary will be defined by several criteria. The thresholded image will be assigned 3-state values of $-1, 0, +1$, corresponding to black, gray, white. Thus, a translating feature in the image will register with equal amounts of black and white in the thresholded image, whereas a contracting or expanding object will manifest itself by an excess of black or white, respectively. Subsequently, each 3-state image is summed up, that is, the gray scale pixel values are added. The result will be numerically proportional only to the amount of contraction or expansion of the objects in the image.

Furthermore, random noise fluctuations will be reduced by the square root of the number of pixels. From such numerical values, derived from one or more simultaneous projections, and with proper calibration procedures, the instantaneous ventricular output, which represents snapshots of flow, can be obtained. If the ventricular pressure signal is simultaneously recorded, the instantaneous load impedance can be computed during the systolic phase by dividing the pressure by the flow.

Referring to FIGS. 3–5, $I_n$ represents examples of a specific instant in time on a specific line section in the image of the heart. $I_{n-1}$ is the corresponding data immediately prior to $I_n$. $I_n - I_{n-1}$ is the subtraction of these two specific lines in the two images.

Determining the difference in magnitude of a given line at two distinct times will permit determination of the extent to which the difference represents heart displacement or heart contraction. For example, the pulsing of power supply 4, (FIG. 1) may be effected at about 30 times per second. Each image may contain approximately 500 lines consisting of 500 pixels each. The pulsing X-ray beam means pulses the X-ray beams at the rate of about 15 to 60 pulses per second, each lasting a few milliseconds. The computation of heart contraction volume occurs for each image frame at one per image frame.

Referring specifically to the example of FIG. 3, $I_n$ is $+4$; $I_{n-1}$ is $+4$ but displaced slightly to the right of $I_n$ in space. When the areas are subtracted $I_n$ produces $+1$ to the left of $I_{n-1}$ and $I_{n-1}$ produces $-1$ to the right of $I_n$. The resultant data sum results in a 0 figure. This shows that pure displacement of the heart results in complete cancellation.

Referring to FIG. 4, pure contraction of the heart is examined. $I_n$ is $+4$ and $I_{n-1}$ is $+2$. The resulting $I_n - I_{n-1}$ result in a $+1$ to the left and a $+1$ to the right. The ultimate summation result being a pure contraction of a $+2$.

FIG. 5 addresses the situation where there is simultaneously both translation and contraction. $I_n$ reads as $+4$. $I_{n-1}$ is displaced to the right and is a $+3$. The resulting $I_n - I_{n-1}$ is a $+2$ to the left and a $-1$ to the right for a $+1$ total. This results in eliminating the translation/movement and yields only the actual contraction of the heart. These numbers can be converted to pumping volume.

Two X-ray sources and image detectors produce pictures of the object from two vantage points projected along axis A and axis B. As used herein "A" and "B," when employed as dimensions, will refer to the distance along the identified axis from the center of the ellipse to the perimeter. If the axes A and B are perpendicular to each other, an approximation of an elliptical shape can be used to compute an area of the cross-section. The area of the ellipse is calculated as $(\pi)(A)(B)$. The depth of the object is axis C. Axes A, B and C are all perpendicular to one another.

Alternatively, for a single projection, an approximation of a circle may be used. In that case, axes A and B would be equal radii.

For purposes of the example, the elliptical shape will be used.

$V_2$ is the volume of the heart when contracted; $V_1$ is the volume of the heart when expanded. The difference between $V_1$ and $V_2$ is the amount of blood pumped by the heart during one beat.

The instantaneous volume $V_t$ of the ventricle will be computed by means of the following formula:

$$V_t = \frac{F\pi}{4} \sum_k^{C_{t-1}} \sum_j^{B_k} b_{jk} \sum_i^{A_k} a_{ik}$$

where $a_{ik}$ and $b_{jk}$ represent the pixels lying within the ventricle in the image plane, and $A_k$ and $B_k$ correspond to the major axes of the ellipses coinciding with the chosen projection planes. C is the length of the ventricle, t refers to the time instant of the image $I_n$ and "t−1" refers to the time instant of the image $I_{n-1}$. In effect, we are computing the area of each ellipse one pixel thick, and obtaining volume by employing height factor C. $\pi = 3.14$, and F is a calibration factor which merely relates the pixel size to the object size in the image.

As we are dealing with the subtracted images with summed pixels, the information from consecutive images represents the changes in A, B, and C. Consequently, the evaluation of A, B, and C will be carried out only once during each cardiac cycle, preferably at end diastole and beginning with electrical systole. This can be determined from the EKG signal. During the rest of the cardiac cycle, the parameters A, B, and C are then expressed in terms of differences dA, dB, and dC as follows:

$$A_t = A_{t-1} - dA_t, \quad B_t = B_{t-1} - dB_t, \quad C_t = C_{t-1} - dC_t$$

where $A_{t-1}$, $B_{t-1}$, and $C_{t-1}$ are the first end diastolic dimensions, and are subsequently decremented as shown above.

Thus, dA, dB and dC each represent the differences in axes A, B and C during the time interval between t-1 and t. Using these variables, the instantaneous volume becomes:

$$V_t = \frac{F\pi}{4} \sum_k^{C_{t-1}-dC_t} (A_{(t-1)k}B_{(t-1)k} - A_{(t-1)k}dB_{tk} - B_{(t-1)k}dA_{tk} + dA_{tk}dB_{tk}).$$

whereas the first end diastolic volume is:

$$V_{t-1} = \frac{F\pi}{4} \sum_k^{C_{t-1}} A_{(t-1)k}B_{(t-1)k}$$

so that the reduction in volume of the heart during contraction becomes:

$$dV_t = \frac{F\pi}{4} \sum_k^{C_{t-1}-dC_t} (A_{(t-1)k}dB_{tk} + B_{(t-1)k}dA_{tk} - dA_{tk}dB_{tk}).$$

Thus, the ventricular output can be computed from initial dimensions and contractions in the three perpendicular dimensions along axes A, B and C.

The ventricular output $dV_t$ thus represents the volume of blood ejected during the time between two sequential snapshot X-ray images, normally 1/30 of a second. Therefore, it is possible to compute 30 times per second the output of the ventricle, corresponding to flow of blood from the left ventricle into the aorta. This flow is propelled by the pressure that the contracting ventricle exerts on the blood.

If this pressure is simultaneously measured in the ventricle by means of a catheter and transducer, the resulting electrical signal can be quantified and recorded.

The simultaneous ratio between the change in the pressure $P_t$ and flow $dV_t$ is defined as the load impedance, in this case for the left ventricle. Thus, the necessary arithmetic operations may be carried out on the flow and pressure signals to yield information on the ventricular load impedance during the systolic phase. To synchronize the pressure and computed flow, the former signal will be properly delayed.

It will be appreciated, therefore, that the present invention provides a method of measuring heart output that uses pulsing X-ray beams through the chest and heart. The portion of the X-ray beam not absorbed by the chest and heart is detected and the X-rays converted into electrical signals. The image signals detected at one time are subtracted from the image signals detected at another time. This is known as time interval differencing or TID. Then, after thresholding and summing of all pixels, the signals relating to heart displacement are cancelled, leaving only the signals relating to heart contraction.

Detection means receive the X-rays from the heart. Digital processors create first digital signals relating to heart contractions at different times. The digital processor subtracts and sums these digital signals so as to effect separation of heart displacement signals and heart contraction signals, permitting rapid automatic computation of volume changes, yielding flow, which in combination with pressure enables computation of impedance.

While for purposes of example and clarity of disclosure, reference has been made herein to use of left ventriculograms, it will be appreciated that any of the heart chambers, including the atria may be employed, if desired.

Whereas particular embodiments of the invention have been described above for purposes of illustration, it will be appreciated by those skilled in the art that numerous variations of the details may be made without departing from the invention as described in the appended claims.

I claim:

1. A method of measuring heart output comprising
   pulsing X-ray beams through a heart chamber containing a contrast medium and blood,
   detecting the portion of said X-rays not absorbed by said heart and chest,
   converting said detected X-rays into electrical signals,
   effecting subtraction of said signals detected at one time from those of another time, and summing the resulting pixel values, whereby said signals relating to heart displacement will be cancelled and said electrical signals relating to heart contraction will remain, and
   converting said heart contraction signals into a corresponding volume of blood pumped by said heart in a predetermined time interval.

2. The method of claim 1 including effecting pixel thresholding and said subtraction and summation by computer means.

3. The method of claim 2 including subsequent to said subtraction and pixel thresholding and summation, displaying the results thereof.

4. The method of claim 1 including employing said method to determine ventricular volume by employing an approximation of a series of ellipses having axes A, B and the series having a height C, proportional to the number of elliptical segments.

5. The method of claim 4 including determining the reduction in volume of the heart by the relationship $$dV_t = \frac{F\pi}{4} \sum_{k}^{C_{t-1}-dC_t} (A_{(t-1)k}dB_{tk} + B_{(t-1)k}dA_{tk} - dA_{tk}dB_{tk})$$

wherein $dV_t$=the reduction in heart volume during the time t and (t-1); t=the instant of the image $I_n$; t-1=the time instant of the image $I_{n-1}$; F=a calibration factor that relates pixel size to heart size in the image; $\pi$=3.14; $A_k$ and $B_k$=the axes A and B of the ellipses at the level k coinciding with the projection planes; C=the length of the ventricle; dA, dB, dC each represent the differences in axes A, B and C, respectively, during the time interval between t-1 and t.

6. The method of claim 5 including pulsing said X-ray beams at a rate of about 15 to 60 pulses/sec each lasting a few milliseconds.

7. The method of claim 5 including computing said heart contraction volume at one per image frame.

8. The method of claim 1 including employing said method to determine ventricular volume by employing an approximation of a series of circles making the axes A and B of equal length and the series having a height C.

9. Apparatus for determining heart output comprising
   X-ray source means for providing at least one pulsed source of X-rays impinging on said heart,
   detection means for receiving said X-rays from said heart,
   processor means for creating digital or analog signals related to heart contractions at different times, and
   said processor means having means for substracting and summing said signals to effect separation of heart displacement signals from heart contraction signals, and
   conversion means for changing said heart contraction signals into information which relates to determining heart output.

10. The apparatus of claim 9 including said processor means having means for converting said heart contraction signals into volume of blood pumped by said heart.

11. The apparatus of claim 10 including display means cooperating with said processor means for displaying information related to said heart contraction signals.

12. Apparatus of claim 11 wherein said processor means including means for determining the reduction in volume of the heart by the relationship $$dV_t = \frac{F\pi}{4} \sum_{k}^{C_{t-1}-dC_t} (A_{(t-1)k}dB_{tk} + B_{(t-1)k}dA_{tk} - dA_{tk}dB_{tk})$$

wherein $dV_t$ = the reduction in heart volume during the time t and t-1; t = the time instant of the image $I_n$; t-1 = the time instant of the image $I_{n-1}$; F = a calibration factor that relates pixel size to heart size in the image; $\pi$ = 3.14; $A_k$ and $B_k$ = the axes of A and B of the ellipses at the level k coinciding with the projection planes; C = the length of the ventricle; dA, dB and dC each represent the difference in axes A, B and C, respectively, during the time interval between t-1 and t.

13. The apparatus of claim 9 including pulse means for pulsing said X-rays at a rate a about 15 to 60 pulses per second.

14. Apparatus for measuring ventricular load impedance in real time comprising

X-ray source means for providing at least one pulsed source of X-rays impinging on said heart, detection means for receiving said X-rays from said heart, processor means for creating digital or analog signals related to heart contractions at different times, said processor means having means for substracting and summing said signals to effect separation of heart displacement signals from heart contraction signals, said processor means having means for converting said heart contraction signals into volume of blood pumped by said heart, and pressure measuring means for providing a reading of blood pressure in the heart chamber, and means for providing the ratio of volume signal to pressure signal thereby defining load impedance.

15. A method of measuring ventricular load impedance in real time comprising pulsing X-ray beams through a heart chamber containing a contrast medium and blood, detecting the portion of said X-rays not absorbed by said heart and chest, converting said detected X-rays into electrical signals, effecting subtraction of said signals detected at one time from those of another time, and summing the resulting pixel values, whereby said signals relating to heart displacement will be cancelled and said signals relating to heart contraction will remain, converting heart contraction signals into a corresponding volume of blood pumped by said heart in a predetermined time interval, determining ventricular pressure, and dividing said ventricular pressure by said volume of blood pumped by said heart.

* * * * *